(12) United States Patent
Marshall et al.

(10) Patent No.: US 6,390,990 B1
(45) Date of Patent: May 21, 2002

(54) BLOOD SAMPLING DEVICE

(75) Inventors: Jeremy Marshall, Oxford; Graham Leslie Underdown, Banbury, both of (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 09/446,825

(22) PCT Filed: Apr. 30, 1999

(86) PCT No.: PCT/GB99/01364

§ 371 Date: Dec. 29, 1999

§ 102(e) Date: Dec. 29, 1999

(87) PCT Pub. No.: WO99/56622

PCT Pub. Date: Nov. 11, 1999

(30) Foreign Application Priority Data

May 2, 1998 (GB) ................................................ 9809355

(51) Int. Cl.⁷ ................................................... A61B 5/00
(52) U.S. Cl. ....................................................... 600/573
(58) Field of Search ............................... 600/573, 576, 600/577, 583; 604/181, 182

(56) References Cited

U.S. PATENT DOCUMENTS

| 4,920,977 | A | | 5/1990 | Haynes |
| 4,959,196 | A | | 9/1990 | Moisson |
| 5,518,006 | A | | 5/1996 | Mawhirt et al. |
| 5,951,492 | A | * | 9/1999 | Douglas et al. .............. 600/583 |
| 6,193,675 | B1 | * | 2/2001 | Krause et al. .............. 600/576 |

FOREIGN PATENT DOCUMENTS

| EP | 0 322 293 | 6/1989 |
| EP | 0 688 532 | 12/1995 |

* cited by examiner

*Primary Examiner*—Kevin Shaver
*Assistant Examiner*—Pamela Wingood
(74) *Attorney, Agent, or Firm*—Young & Thompson

(57) ABSTRACT

A blood sampling device has a barrel enclosing a lancet and a spring urging the lancet rearwardly. A dual purpose container fits the rear end of the barrel and its first function is to be pushed forwards relative to the barrel to project the tip of the lancet. A shearable bridge breaks when sufficient pressure is applied, allowing the lancet to retract. The device is then reversed to present the rear end of the container to the drawn blood, which is absorbed thereby. The container with sample for analysis is removed from the barrel which, when the lancet safe inside, can be discarded.

8 Claims, 3 Drawing Sheets

BLOOD SAMPLING DEVICE

BACKGROUND OF THE INVENTION

This invention relates to blood sampling devices, and it is particularly concerned with devices suitable for use on large animals, such as cattle, with thick hides.

To take a sample, first it is necessary to draw blood from as small an incision as possible, and then to collect the drop or drops that then appear as quickly as possible, avoiding contamination. While the sample will then have to be conveyed from farm to laboratory, the actual pricking implement should be made safe and disposable.

It is the aim of this invention to provide a device where these features are combined.

SUMMARY OF THE INVENTION

According to the present invention there is provided a blood sampling deice comprising a hollow barrel housing a pricker urged toward a retracted position from a forward end of the barrel by spring means, and a container that co-operates with the rear end of the barrel, the container forming an operating member which is pressed in the forward direction to project the pricker from the barrel, being adapted to collect and contain the blood sample derived from the pricker, and being separable from the barrel to convey the sample elsewhere, the barrel with the pricker retracted by the spring means being disposable.

Preferably, the barrel is integrally moulded in plastics material in two halves mutually hinged about a longitudinal axis, the halves then being closed around the spring means and pricker to provide guide means for the pricker.

Conveniently the container when serving as the operating member, acts on an element connected to the pricker by a shearable bridge, this bridge breaking as pressure greater than that which ensures full penetration of the pricker is applied. The user can sense the breakage by the container shooting forward in relation to the barrel, and in completing its travel it gives a final push to the barrel.

The barrel, on closure, can be structured to form two diametrically opposed longitudinal slots in which are received wings of said element, allowing longitudinal but not rotational movement thereof. Preferably, the tip of the pricker on manufacture is embedded in a twist-off cap integrally moulded with the body of the pricker, the cap initially being external of the forward end of the barrel and keeping the pricker in a forward position with the spring means energised. The restraint on rotation allows the twist-off action to be carried out easily, and it is only then that the pricker can retract ready for use.

Preferably, the container is guided by the barrel and has a hollow compartment with a closed forward end projecting into the barrel to act on said pricker. It therefore acts like a piston rod. The compartment will contain an absorbent filling accessible through its rear end to soak up the blood sample when the pricker has been withdrawn and the device reversed. The container will have a closure cap for the rear end of the compartment, and as soon as a sample is taken, the cap is closed over and the container removed from the barrel.

The container conveniently has a snap engagement with the barrel.

BRIEF DESCRIPTION OF THE DRAWINGS

For a better understanding of the invention, one embodiment will now be described, by way of example, with reference to the accompanying drawings in which.

DETAIL DESCRIPTION OF THE PREFERRED EMBODIMENTS

Figure 1:
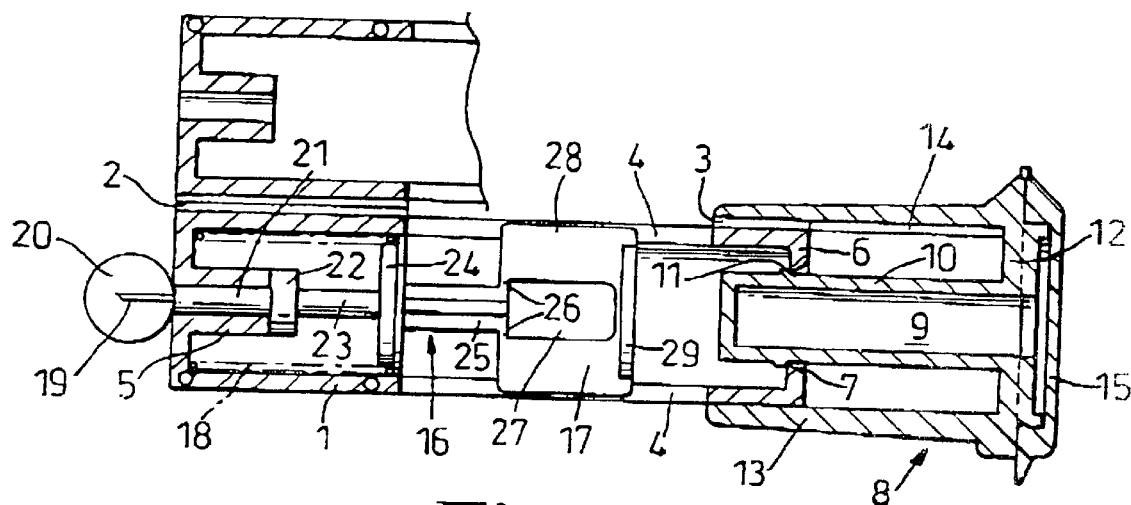
FIGS. 1 to 6 are axial sections of a blood sampling device in various stages from first assembly to completed use.

The device has a generally cylindrical barrel 1 of plastics material moulded in two symmetrical halves with a longitudinal split and connected by flexible webs 2 and 3 at opposite ends by which the two halves can be hinged together before being secured. Along intermediate portions of the straight edges between the webs 2 and 3 there are shallow recesses which, on completion of the barrel, form axially parallel slots 4. The forward end of the barrel, to the left as seen in the figures, is closed apart from a central aperture at the mouth of a tubular re-entrant guide 5. At the rear end of the barrel an inwardly projecting flange 6 has a tapered rim around the aperture 7 which it forms.

A container 8, also of moulded plastics material, fits to the rear end of the barrel 1. It has a cylindrical compartment 9 formed by a tubular portion 10 with a closed forward end. Set back from this end there is a shallow external annular rib 11 of rounded cross section which allows the tubular portion 10 to be snapped through the aperture 7. At the rear end, the tubular portion 10 opens into the centre of a disc 12, and projecting forwardly from the periphery of this disc there is a generally cylindrical skirt 13 which closely fits the outside of the barrel 1. There is a longitudinal groove 14 within this skirt to accommodate the web 3 which, when the barrel parts are closed together, forms a spline. A cap 15 is hinged by an integral web to the disc 12 and can be snapped into the closed position as shown in most of the figures.

The compartment 9 will contain an absorbent pad, which will extend right to its mouth.

The barrel 1 houses a lancet 16, a piston 17 and a coil spring 18. The lancet has a body moulded around a needle whose tip 19 is initially shrouded by a cap 20. This cap is moulded integrally with the lancet body but it can be twisted off to expose the needle tip.

The body of the lancet has, from the leading end, a forward shaft portion 21 which fits snugly in the guide 5, a collar 22, a central shaft portion 23, a disc 24 with a stepped periphery of a diameter close to that of the interior diameter of the barrel, and a rear shaft portion 25. The latter is integrally connected at its rear end to the piston 17 by thin bridges 26 at the mouth of a central recess 27 in a diametral plate 28 projecting forwardly from a co-axial disc 29. The disc closely fits within the barrel, and the longitudinal edge portions of the plate 28, which are proud of the circumference of the disc 29, fit the slots 4.

Instead of two bridges 26, it may be possible to have just one.

The device is assembled as shown in FIG. 1 with he lancet 16 located by the portion 21 in the guide 5 and with the springs 18, acting between the forward end of the barrel and the periphery of the disc 24, slightly compressed. The cap 20 engaging the mouth of the guide 5 holds the lancet 16 in this position. The two parts of the barrel are closed together and secured, and then the container 8 is fitted to the rear end.

Figure 2:
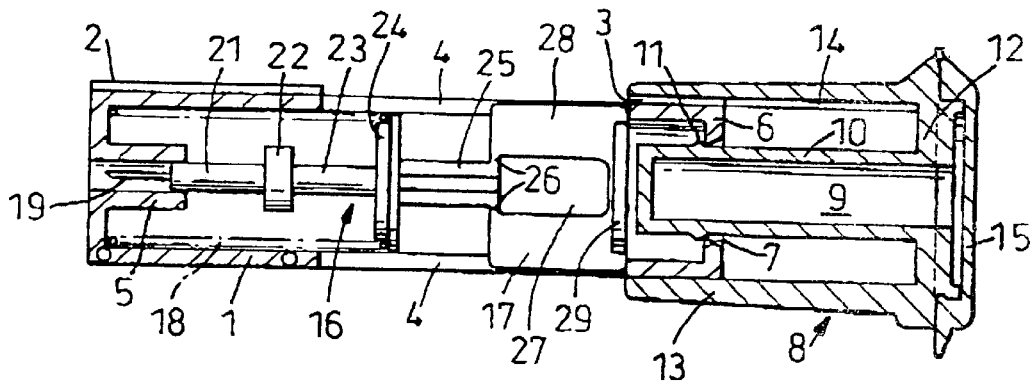

To prime the device ready for use, the cap 20 is twisted off. The rest of the lancet will not rotate, since it is held against that by the edge portions of the plate 28 in the slots 4. But the lancet is released to be urged rearwardly by the spring 18 until arrested by the plate 28 hitting the rear end of the slots 4, as seen in FIG. 2.

Figure 3:
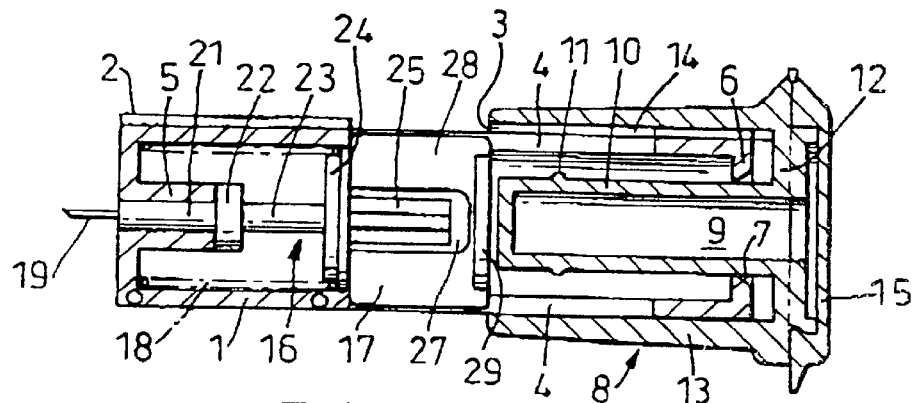

The forward end is then placed against the animal and the container 8 is urged forward by pressing on the cap 15. This, acting through the portion 10, the piston 17 and the lancet 16, will cause the needle tip 19 to project until halted by the collar 22 coming up against the rear end of the guide 5. But then further or continued pressure is applied, sufficient to break the bridges 26. The piston 17 shoots forward while the portion 25 enters the recess 27. The piston is arrested by the plate 28 coming up against the forward ends of the slots 4, as shown in FIG. 3. This final shove ensures good penetration.

Figure 4:
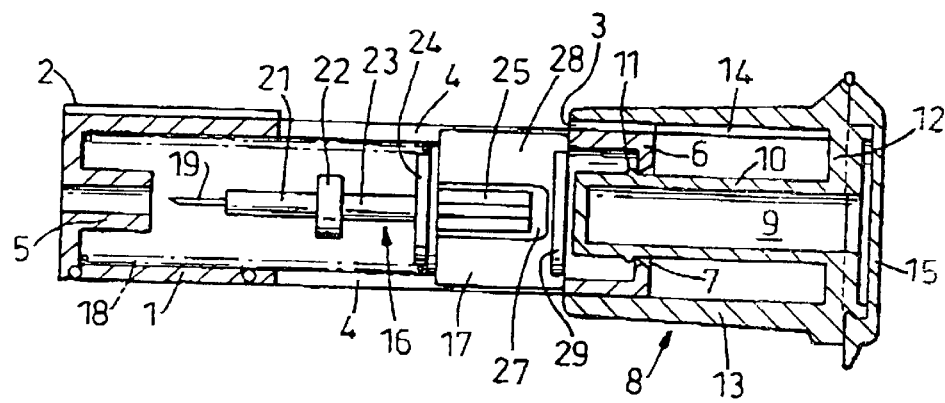
Figure 5:
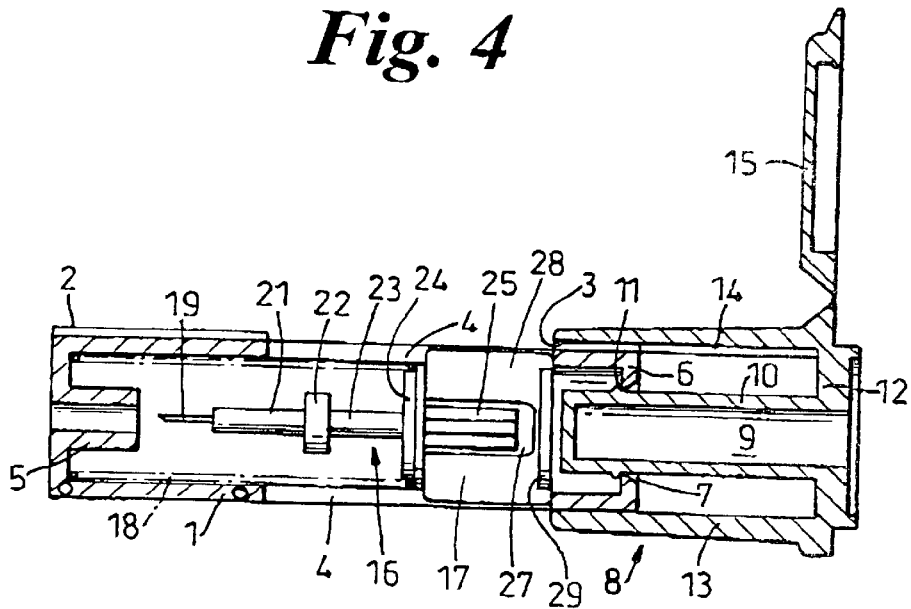
Figure 6:
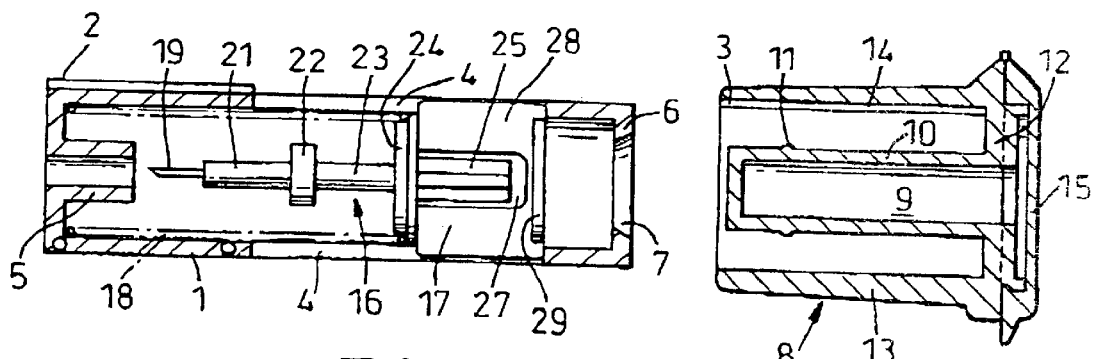
Figure 7:
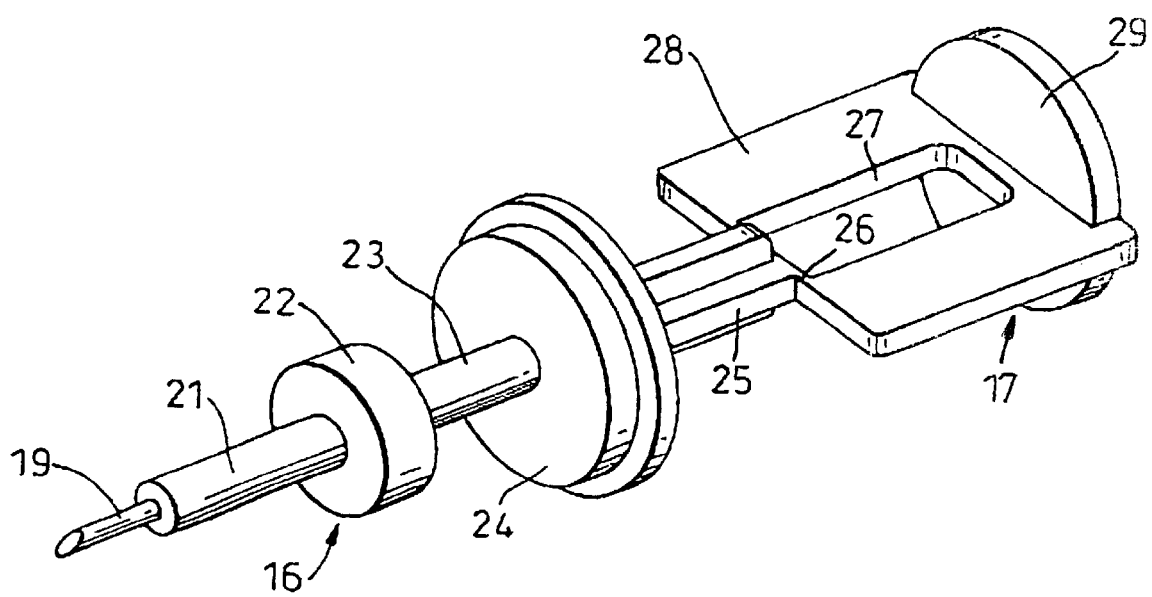
FIG. 7 is a perspective view of a lancet forming part of the device.

The device is then pulled away from the animal, and the spring 18 can exert itself to push the lancet 16 back into the body. The piston 17 and the container 8 are also pushed back by this action, until the plate 28 reaches the rear ends of the slots 4. The device is then in the FIG. 4 position with the needle tip 19 retracted beyond the guide 5 and the rib 11 back against the lip of the aperture 7.

The cap 15 is then opened and the device turned round for the mouth of the compartment 9 to be presented to the blood that will have appeared as a result of the pricking action. The disc 12 is pressed against the animal's skin around the puncture, and the blood will be soaked up by the absorbent pad in the compartment 9. As soon as the device is taken away the cap 15 can be closed over, sealing the sample in the container 8.

Finally, the container is snapped clear of the barrel 1, and the latter can be safely thrown away while the container can convey the sample to a laboratory for analysis.

We claim:

1. A blood sampling device comprising a hollow barrel housing a pricker urged towards a retracted position from a forward end of the barrel by spring means, and a container that co-operates with the rear end of the barrel, the container forming an operating member which is pressed in the forward direction to project the pricker from the barrel, being adapted to collect and contain the blood sample derived from the pricker, and being separable from the barrel to convey the sample elsewhere, the barrel with the pricker retracted by the spring means being disposable.

2. A blood sampling device as claimed in claim 1, wherein the barrel is integrally moulded in plastic material in two halves mutually hinged about a longitudinal axis, the halves then being closed around the spring means and pricker to provide guide means for the pricker.

3. A blood sampling device as claimed in claim 1, wherein the container, when serving as the operating member, acts on an element connected to the pricker by a shearable bridge, this bridge breaking as pressure greater than that which ensures full penetration of the pricker is applied.

4. A blood sampling device as claimed in claim 3, wherein the barrel, on closure, forms two diametrically opposed longitudinal slots in which are received wings of said element, allowing longitudinal but not rotational movement thereof.

5. A blood sampling device as claimed in claim 4, wherein the tip of the pricker on manufacture is embedded in a twist-off cap integrally moulded with the body of the pricker, the cap initially being external of the forward end of the barrel and keeping the pricker in a forward position with the spring means energised.

6. A blood sampling device as claimed in claim 1, wherein the container is guided by the barrel and has a hollow compartment with a closed forward end projecting into the barrel to act on said pricker, like a piston rod, the compartment containing an absorbent filling accessible through its rear end to soak up the blood sample when the pricker has been withdrawn and the device reversed.

7. A blood sampling device as claimed in claim 6, wherein the container has a closure cap for the rear end of the compartment.

8. A blood sampling device as claim in claim 1, wherein the container has a snap engagement with the barrel.

* * * * *